United States Patent [19]

Strawn

[11] Plant 4,898

[45] Oct. 26, 1982

[54] MINIATURE ROSE PLANT

[76] Inventor: Leslie E. Strawn, 10422 Morningside Ave., Garden Grove, Calif. 92643

[21] Appl. No.: 241,759

[22] Filed: Mar. 9, 1981

[51] Int. Cl.[3] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant characterized by its blended pink shades of buds and flowers of distinctive form and further indentified by the erect, dwarf, and compact plant.

1 Drawing Figure

1

The present invention relates to a new and distinct variety of hardy, dwarf, bush type rose plant of the miniature class; the variety being primarily characterized — as to novelty — by the blended pink shades of buds and flowers which in general color effect are similar to Stacey Sue (miniature — U.S. Plant Pat. No. 4,158).

The variety is further characterized by:

The unique buds and flowers.

An abundance of bloom, with the flowers borne one to a stem. No side buds.

A light sweet fragrance.

A plant which is vigorous, of an upright and rounded shape with small semi-glossy foliage and pointed leaflets; the buds and flowers having the form and size similar to Peaches 'N Cream (miniature — U.S. Plant Pat. No. 4,278).

The plant, which has a normal height of 10 to 12 inches, can easily be maintained by occasional trimming.

A plant which grows and blooms satisfactorily both in a greenhouse and outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between Tiki (floribunda non-patented) as the seed parent and Baby Betsy McCall (miniature — U.S. Plant Pat. No. 1,984 expired) as the pollen parent.

Subsequent to origination of the variety I successfully asexually reproduced it in my garden, located as foresaid (also propagated by Pixie Treasures Rose Nursery, 4121 Prospect Ave., Yorba Linda, Orange County, Calif.), by cuttings as well as by budding; the reproductions having run true in all respects.

The color photograph illustrates the variety, including the foliage, buds and flowers.

Referring now specifically to the new and distinct variety of miniature rose plant, the following is a detailed description thereof in outline; all major color plate indentifications being by reference to the British Colour Council Horticultural Colour Chart, except where common terms of color definition are employed.

Type: Hardy; dwarf; bushy; upright; seedling; greenhouse; outdoors; cut flowers; garden decoration; pot plant.

Class: Miniature.

2

*Variety name.*—Whimsical.

Flowers borne: Singly on upright slender stems.

Quantity of bloom: Abundant, both outdoors and in greenhouse.

Bud:

*Peduncle.*—Medium length, $2\frac{1}{2}$ to $3\frac{1}{2}$ cm; slender and sturdy; erect; slight curve; light green, usually tinted bronze (outdoors);

*Hairs.*—Microscopic if any; few glands.

*Before calyx breaks.*—Size — small (2 cm length, may vary). Form — pointed; foliaceous parts extend beyond tip $\frac{1}{3}$ or more than its length. Color — medium green.

*As calyx breaks.*—Color of outside petals showing near Porcelain Rose 620/3. Opening — opens well in all weather; unfurls slowly.

Bloom:

*Size when fully open.*—Small, averaging about 4 cm.

*Petalage.*—Double — averaging about 35 to 40 petals, arranged symmetrically, plus 5 or 6 petaloids.

*Form.*—Pointed bud with high center; as petals unfurl symmetrically the flower retains its center form; outside petals curling downward at sides, giving a distinct pointed effect to the perimeter.

Petals: Fairly thick and of good substance; smooth and satiny on both surfaces.

*Shape.*—Outside petals — broad heart shaped with pointed tip and blunt base; intermediate petals — heart shaped with pointed tip, slightly smaller, blunt base; inside petals — oval with pointed tip and pointed base; petaloids — 5 or 6 with one or two among the stamens.

Color: One half to three quarters open flower from a plant grown outdoors at Pixie Treasures Rose Nursery, Yorba Linda, Calif., October 1980.

*Outside petal.*—Outside surface — edge of petal (outer 3 mm) near Empire Rose 0621/1; center area near Porcelain Rose 620/3; base faint greenish yellow; guard petal may be streaked with a very fine line of pink similar to Empire Rose 0621/1 which can be 3 to 4 mm length or be absent or in the shape of a minute triangle or blotch. Inside surface — outer edge of petal very near Porcelain Rose 620/1, then blends gradually to the center becoming almost Porcelain Rose 620/3 or paler, base lightly touched with a pale yellow green.

*Intermediate petal.*—Outside surface — outer edge of petal near Empire Rose 0621/1 then fading toward center area to almost Empire Rose 0621/3; center area near Porcelain Rose 620/1 with an undertone of pale yellow similar to Naples yellow 403; at the base the Porcelain Rose shade fades leaving a pale yellow tip. Inside surface — outer ⅓ of area near Empire Rose 0621/2 fading toward center where undertone of Naples Yellow becomes dominant and continues to base. The blending of the shades of Empire Rose with the undertones of Naples Yellow give an overall effect near French Rose 520/1 or 520 to the intermediate petals before they have unfurled into a full blown flower.

*Inner petal.*—Outside surface — outer half of area brushed with Porcelain Rose close to 620/1 blending to near Porcelain Rose 620/2 toward base; base close to Naples Yellow 403. Inside surface — outer half of area brushed with Porcelain Rose close to 620/2 becoming less dominant as base shade of near Naples Yellow 403/2 shows through and colors petal to base.

General color effect:

*Newly opened flowers.*—Symmetrical arrangement of light pink petals of the tones and tints of Porcelain Rose and Empire Rose. The blending of the undertones of Naples Yellow toward the center of the flower create a shade of coral-pink in that area. The amount of yellow tints and undertones vary from flower to flower so that there can be very different looking blooms in their coloring on the same plant.

*Three days open.*—Yellow undertones fade leaving a bloom of pink and creamy white with stamens showing.

Behavior: Opens well in all weather. Spent petals tend to hang on for a few days becoming darkened from weather and sunlight; petals fall, then calyx and peduncle dries and falls. Flower longivity (October 1980) — plant in pot 4 to 5 days; in the ground may last longer. Cut flowers at living room temperature 3 to 4 days or longer.

Reproductive organs:

*Stamens.*—Vary 25–30.

*Filaments.*—Pale greenish white, uneven lengths.

*Anthers.*—Golden yellow, 1 mm, introse, few turning sideways.

*Pollen.*—Moderate amount.

*Pistils.*—Project above disc.

*Styles.*—Several, bunched, 3 to 4 mm length, dark pinkish.

*Ovaries.*—Enclosed in calyx.

*Hips.*—Rarely formed, if ever.

*Sepals.*—Permanent, spear shaped, reflexed.

*Seeds.*—None.

Foliage:

*Leaves.*—Compound of five leaflets, 5 to 7 cm length; moderate substance; semi-glossy.

*Leaflets.*—Shape — broad lanceolate, broad apex; not supported by a petiolule.

*Rachis.*—Medium length, upper side deeply grooved: underside — few minute thorns or thornless.

*Stipules.*—Short with slender pointed auricles flairing outward at approx. 45 degrees.

*Color.*—Medium green; serrated edges and rachis tending to be reddish bronze on older leaves as well as new growth.

Growth:

*Habit.*—Dwarf; upright; height 25 to 30 cm (10–12 in.).

*Growth.*—Vigorous: internodes short: much branched.

*Canes.*—Slender; sturdy.

*Main stems.*—Color — medium green.

*Branches.*—Medium green, tinted bronze at times.

*Thorns.*—Thornless.

*Young shoots.*—Reddish green.

The miniature rose plant and its flowers as herein described may vary in slight detail due to climatic, soil and cultural conditions under which the variety may be grown.

The following is claimed:

1. A new and distinct variety of miniature rose plant of hardy, dwarf, bushy, upright, much branched habit, substantially as illustrated and described, characterized by buds and flowers which are in a color hue similar to Stacey Sue (miniature — U.S. Plant Pat. No. 4,158) giving a coloring effect of blended shades of pink with coral undertones and resembling Peaches 'N Cream (miniature — U.S. Plant Pat. No. 4,278) in form and size, having buds and flowers of a distinct and unusual appearance as compared to other miniature rose plants; said flowers being fully double, uniquely formed with high centers; and further characterized by its vigor, abundant foliage and ease of propagation from soft wood cuttings and by budding, and with an abundance of flowers.

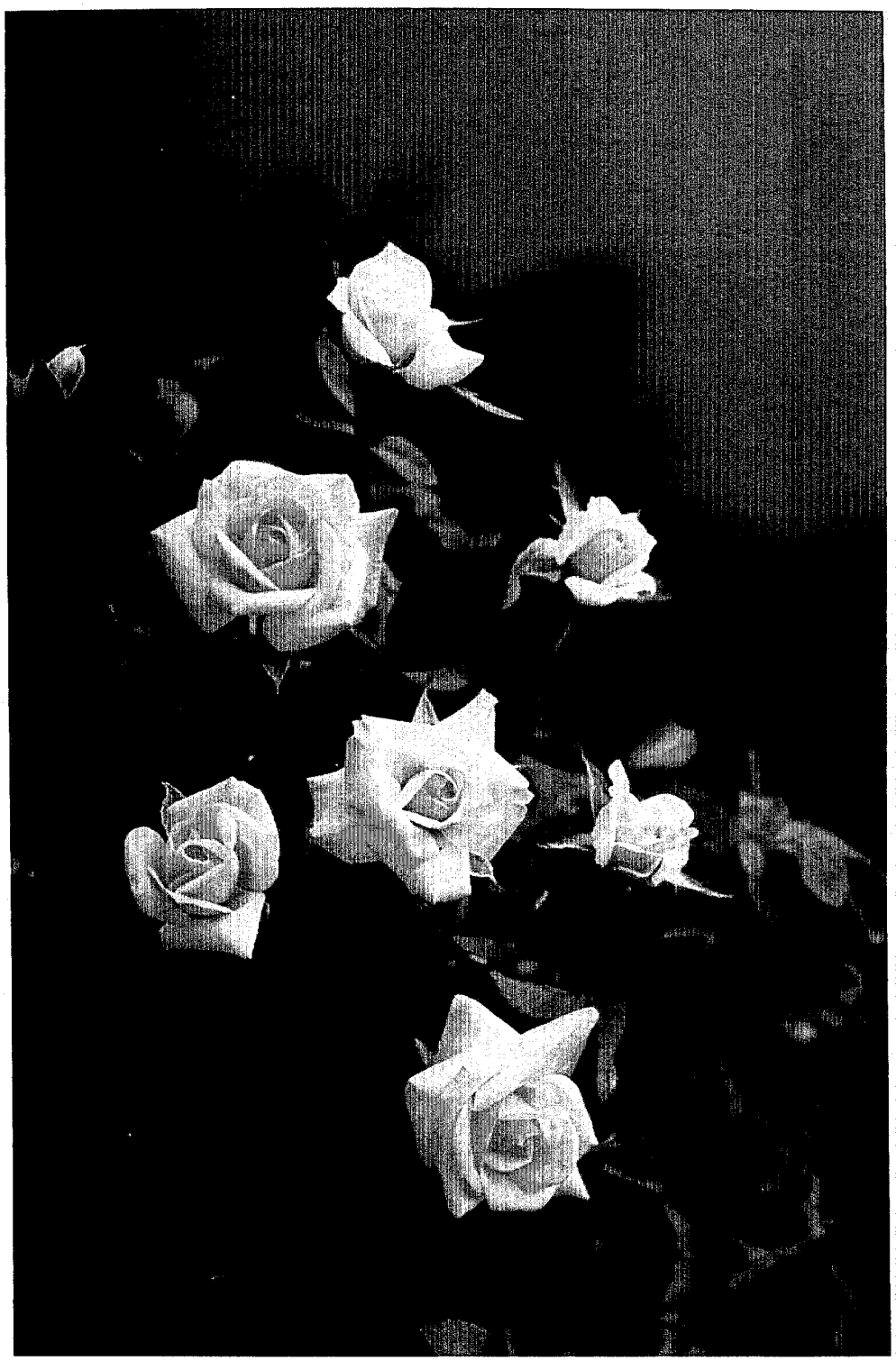

* * * * *